United States Patent
Bharati et al.

(10) Patent No.: US 10,512,484 B2
(45) Date of Patent: Dec. 24, 2019

(54) EPILATION DEVICE

(71) Applicant: Asani Threading Inc., Toronto (CA)

(72) Inventors: Subodh Bharati, Toronto (CA); Sivashanthan Sivapalan, Toronto (CA)

(73) Assignee: Asani Threading Inc.

( * ) Notice: Subject to any disclaimer, the term of this patent is extended or adjusted under 35 U.S.C. 154(b) by 255 days.

(21) Appl. No.: 15/021,025

(22) PCT Filed: Sep. 12, 2014

(86) PCT No.: PCT/CA2014/050862
§ 371 (c)(1),
(2) Date: Mar. 10, 2016

(87) PCT Pub. No.: WO2015/035516
PCT Pub. Date: Mar. 19, 2015

(65) Prior Publication Data
US 2016/0220273 A1 Aug. 4, 2016

(30) Foreign Application Priority Data
Sep. 13, 2013 (CA) ..................... 2826951

(51) Int. Cl.
*A61B 17/50* (2006.01)
*A45D 26/00* (2006.01)

(52) U.S. Cl.
CPC .............. *A61B 17/50* (2013.01); *A45D 26/00* (2013.01)

(58) Field of Classification Search
CPC ................ A45D 26/00; A45D 26/0042; A45D 26/0047–0052; A45D 26/0057; A61B 2017/00752
See application file for complete search history.

(56) References Cited

U.S. PATENT DOCUMENTS

| 4,983,175 A | 1/1991 | Daar et al. |
| 5,643,287 A | 7/1997 | Ahad |

(Continued)

FOREIGN PATENT DOCUMENTS

| EP | 270222 A1 | 6/1988 |
| GB | 225445 A | 12/1924 |

(Continued)

OTHER PUBLICATIONS

The International Search Report and Written Opinion of the International Search Authority dated Oct. 23, 2014 for the corresponding International Application No. PCT/CA2014/050862, 12 pages.

*Primary Examiner* — Katherine M Shi
*Assistant Examiner* — Lindsey Bachman
(74) *Attorney, Agent, or Firm* — Banner & Witcoff, Ltd.

(57) ABSTRACT

A hand-held epilation device for removal of unwanted hair by a user which includes a body portion, arm, slider mechanism, and a rotatable flexible member. The slider mechanism is held under tension. The rotatable flexible member is held under tension and rotates which coils and uncoils two portions of the rotatable flexible member to grasp and remove unwanted hairs. The slider mechanism moves along the arm to maintain a consistent angle between two portions of the rotatable flexible member allowing one portion of the rotatable flexible member to act as an aid to help the user target removal of unwanted hair and permitting more precise hair removal.

7 Claims, 9 Drawing Sheets

(56) References Cited

U.S. PATENT DOCUMENTS

| | | | |
|---|---|---|---|
| 5,908,425 A | 6/1999 | Adam | |
| 5,951,573 A | 9/1999 | Yashar | |
| 7,235,085 B1 | 6/2007 | Tahir | |
| 2010/0185213 A1* | 7/2010 | Lam | A45D 26/00 606/131 |

FOREIGN PATENT DOCUMENTS

| | | | | |
|---|---|---|---|---|
| GB | 2461878 A | | 1/2010 | |
| WO | 2006105011 A2 | | 10/2006 | |
| WO | 2008002033 A1 | | 1/2008 | |
| WO | 2008143656 A2 | | 11/2008 | |
| WO | WO 2011/115584 | * | 9/2011 | A45D 26/00 |

* cited by examiner

EPILATION DEVICE

The present application is a U.S. National Phase Application under 35 U.S.C. § 371 and applicant herewith claims the benefit of priority of PCT/CA2014/050862 filed Sep. 12, 2014, which claims priority to Canadian Application 2826951, filed Sep. 13, 2013, which is incorporated by reference herein in its entirety.

FIELD OF THE INVENTION

The present invention generally relates to epilation devices. More particularly, the present invention relates to a powered epilation device for removal of hair.

BACKGROUND OF THE INVENTION

Devices and methods for selective hair removal have long existed in the fields of cosmetology and medicine. Wax based preparations are widely used to remove body and facial hair. Cold wax techniques have limited effectiveness, and hot wax preparations are typically painful to apply and can be damaging to the skin. Chemical depilatories can also be damaging to human skin tissue. Epilators such as tweezers are time consuming, while powered epilators are cumbersome and lack precision.

Threading is a method of hair removal that originates from an ancient practice of using thread to remove hair. Two lengths of threads are first manually twisted and placed along a row of unwanted hair. By manipulating the thread at four points, unwanted hair is grasped and pulled from the follicle. As compared to wax or chemical depilatories, threading is gentler on the skin and provides more precise hair removal. It is also much more effective for eyebrow shaping than any other method of facial hair removal including other epilation methods such as tweezing and waxing.

There have been various attempts to provide threading devices for a user to remove unwanted hair. Devices typically employ mutual twisting of two threads, or winding a thread portion around a fixed thread portion. Such devices are not optimal because they are large and unwieldy which obstructs a user when removing hair from difficult to reach areas, such as under the eyebrows. When one thread portion is wound around the fixed thread portion, the fixed thread portion is pulled away from its initial position which further compromises precise hair removal.

Therefore, it can be appreciated that there exists a need for a device that allows a user to more precisely remove unwanted hair from difficult to reach areas.

SUMMARY OF THE INVENTION

According to a first aspect of the invention, an epilation device is provided for removal of unwanted hair by a user. The device has a body portion, an arm, a slider mechanism held under tension and a rotatable flexible member held under tension. The rotatable flexible member has a first and a second portion, and is connected to the arm at one end and the slider mechanism at the other end. The rotatable flexible member is held under tension with the first portion held under greater tension than the second portion. When the rotatable flexible member rotates, first and second portions of the rotatable flexible member coil and uncoil relative to the direction of rotation along the first portion of the rotatable flexible member and tension in the rotatable flexible member varies. The slider moves to adjust for the varying tension in the rotatable flexible member portions, thereby guiding the second portion of the rotatable flexible member to maintain a consistent angle relative to the first portion of the rotatable flexible member. The coiled rotatable flexible member deviates minimally from the initial position of the first portion of the rotatable member which serves as a guide for precise hair removal.

The device may further include a pivot mechanism that serves to connect the rotatable flexible member to the arm and balance varying tension of the rotatable flexible member.

A rotational element may also be added to connect the rotatable flexible member to the arm to reduce torsional tension build up in the rotatable flexible member.

The slider mechanism may be held under tension by a tension control mechanism.

According to a second aspect of the invention, an epilation device is provided for removal of unwanted hair by a user. The device has a body portion, an arm, a rotatable rod held under tension, and a rotatable flexible member held under tension. The rotatable flexible member has a first and a second portion with the first portion held under greater tension, and is connected to the arm at one end and the rotatable rod at the other end. The second portion of the rotatable flexible member is coiled around the rotatable rod. When the rotatable flexible member rotates, first and second portions of the rotatable flexible member coil and uncoil relative to the direction of rotation along the first portion of the rotatable flexible member and tension in the rotatable flexible member varies. The rotatable rod rotates to adjust for the varying tension in the rotatable flexible member and uncoils and coils the second portion of the rotatable flexible member along the length of the rotatable rod to guide the second portion of the rotatable flexible member to maintain a consistent angle relative to the first portion of the rotatable flexible member. The coiled rotatable flexible member deviates minimally from the initial position of the first portion of the rotatable flexible member which serves as a guide for precise hair removal.

A rotational element may also be provided to connect the rotatable flexible member to the arm to reduce torsional tension build up in the rotatable flexible member.

The rotatable rod may be held under tension by a tension control mechanism.

According to a third aspect of the invention, an epilation device is provided for removal of unwanted hair by a user. The device has a body portion, an arm, a rotatable rod, a rotational mechanism and a rotatable flexible member. The rotatable flexible member has a first and a second portion. The first and second portion of the rotatable flexible member are coiled and connected to the rotational mechanism on one end, the second portion of the rotatable flexible member is looped over the rotatable rod and the first and second portion of the rotatable flexible member are connected to the arm on the other end, the rotatable flexible member is held under tension with first portion held under greater tension than the second portion. When the rotatable flexible member rotates, first and second portions of the rotatable flexible member coil along the first portion of the rotatable flexible member at one end and tension in the rotatable flexible member varies. At the same time, the first and second portions of the rotatable flexible member uncoil at the other end to reduce any tension build up in the rotatable flexible member and thereby moves the looped second portion of the rotatable flexible member along the length of the rotatable rod to guide the second portion of the rotatable flexible member to maintain a consistent angle relative to the first portion of the rotatable flexible member. The coiled rotatable flexible member deviates minimally from the initial position of the first portion of the rotatable flexible member which serves as a guide for precise hair removal.

DETAILED DESCRIPTION

An epilation device is provided for precise hair removal. This invention provides mechanisms to maintain a consistent angle between two rotatable flexible member portions, and minimize deviation of a first rotatable flexible member portion, held under greater tension, from its initial position when first and second rotatable flexible member portions are coiled. This allows the first rotatable flexible member portion to serve as a guide to help a user position the rotatable flexible member portions to more precisely remove unwanted hair, including difficult to reach areas such as under the eyebrows.

One possible arrangement of such mechanisms to minimize deviation and maintain a consistent angle is through the utilization of a slider mechanism as shown in FIGS. 1 to 8. As the slider mechanism moves along the length of the device, a consistent angle between the two rotatable flexible member portions is maintained and deviation of the first rotatable flexible member portion from its initial position is minimized. The slider mechanism includes any mechanism that moves along the length of the device in correspondence with the direction of the coiling and uncoiling of the rotatable flexible member portions.

Figure 1:
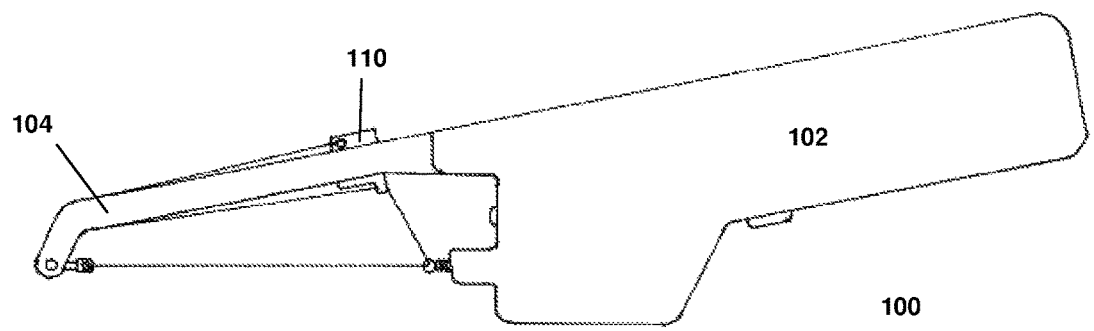
FIG. 1 is a side view of a first embodiment of the epilation device.
Figure 2:
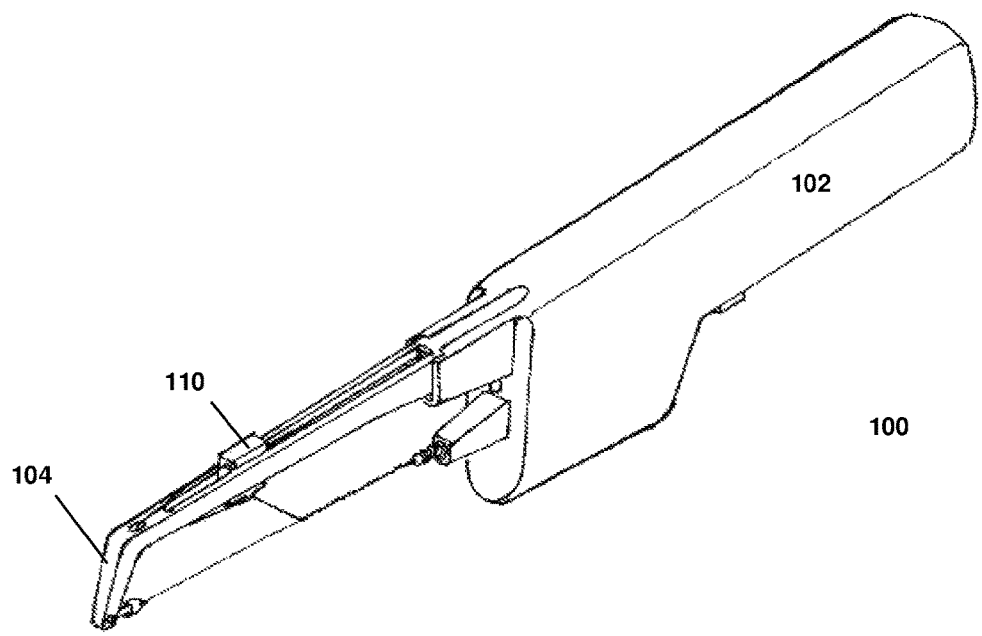
FIG. 2 is a perspective view of the epilation device of FIG. 1.
Figure 3:
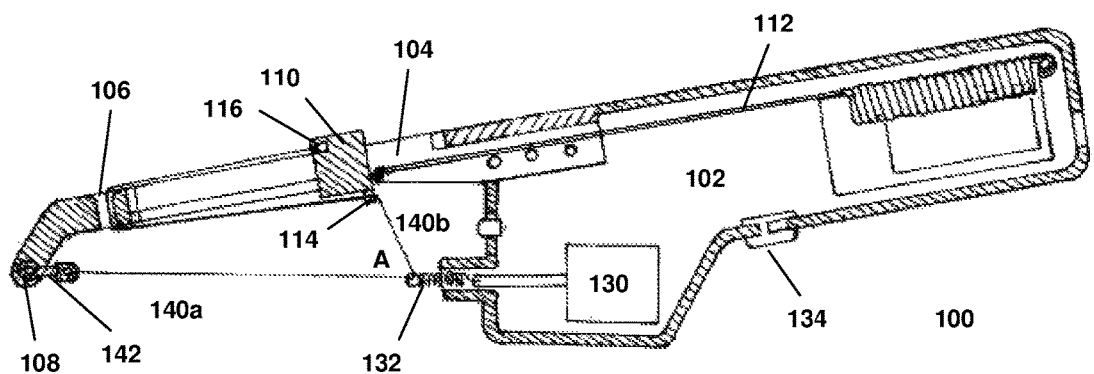
FIG. 3 is a side cross-sectional view of the epilation device of FIG. 1.
Figure 4:
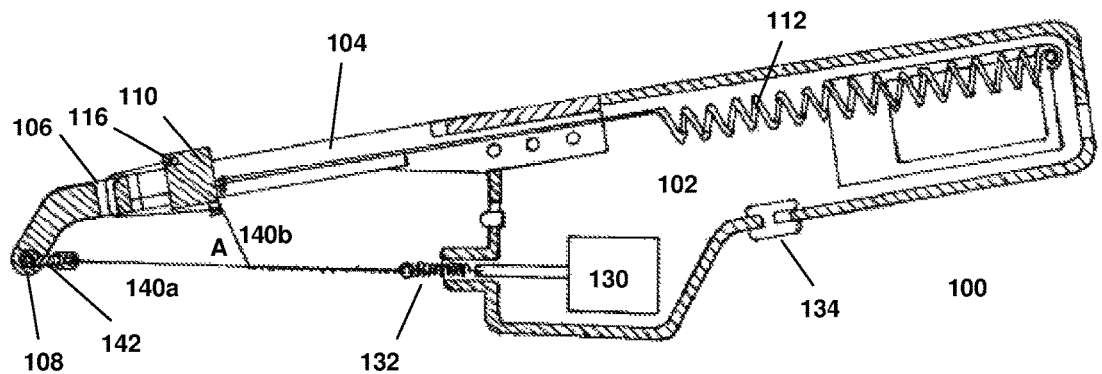
FIG. 4 is a side cross-sectional view of the epilation device of FIG. 1.

FIGS. 1 and 2 illustrate side and perspective views of a first embodiment of an epilation device 100. The epilation device 100 includes a hand-held body portion 102 and an arm 104 connected to the body portion 102. FIGS. 3 and 4 are cross-sectional side views of the epilation device 100. A slider mechanism 110 is coupled to the arm 104 and movable along the length of the arm 104. The slider mechanism is held under tension by a slider biasing element 112 disposed within the body portion 102. A biasing element is defined as any material with elastic properties or other mechanisms including but not limited to, springs, elastic cords, and rubber bands, gears or a combination thereof. The slider biasing element 112 is connected to the slider mechanism 110 to regulate movement of the slider mechanism.

A rotatable flexible member is held under tension by biasing element 132. One end of the rotatable flexible member is connected to the distal end of the arm at arm connection point 108. The rotatable flexible member is then connected to biasing element 132 to form a first portion of the rotatable flexible member 140a. The biasing element 132 regulates tension of the rotatable flexible member 140a. The rotatable flexible member is passed through slider opening 114 on a lower portion of the slider mechanism 110 to form a second portion of the rotatable flexible member 140b. The rotatable flexible member 140b is further passed through an opening 106 in the arm 104 and the other end of the rotatable flexible member 140b is connected to the slider mechanism 110 at a slider connection point 116. The rotatable flexible member is connected such that rotatable flexible member 140a has greater tension than rotatable flexible member 140b. This ensures the coiling of rotatable flexible members 140a and 140b deviates minimally from the initial position of rotatable flexible member 140a and allows rotatable flexible portion 140a to serve as a guide for precise hair removal.

The rotatable flexible member is defined as any thin wire like material including but not limited to threads. The first portion and second portion of the rotatable flexible member may be portions of a single length of the rotatable flexible member, or may be two separate lengths of rotatable flexible members.

The rotatable flexible member is rotatable by a rotational mechanism 130. The rotational mechanism is defined as any mechanism that conveys rotational motion by means of manual or electrical power source or a combination thereof. The rotational mechanism 130 for conveying rotational motion is disposed within the body 102 and connected to a biasing element 132. The rotational mechanism 130 is comprised of a motor, electronics and a power source to provide bidirectional rotation. A trigger mechanism 134 to control the rotational mechanism 130 is accessible from the outside of the body portion 102.

Different arrangements of the rotational mechanism, biasing elements and trigger mechanisms are possible. The rotational mechanism may be disposed within the body, partially disposed within the body or located outside of the body. The biasing element 132 may be connected to the distal end of the arm rather than the rotational mechanism 130. The biasing element 132 may also be connected to rotational mechanism 130 within the body and the rotatable flexible member connected directly to the rotational mechanism 130. The trigger mechanism may be located elsewhere on the device or separate from the device.

FIGS. 1 and 3 show the epilation device 100 in an initial position. A user positions the epilation device 100 such that the rotatable flexible members 140a and 140b are positioned on the user's skin over hair that is to be removed. The rotatable flexible member 140a is used as a guide for precise hair removal. When a user activates trigger mechanism 134, rotational mechanism 130 rotates in one direction causing rotatable flexible members 140a and 140b to coil. When the rotatable flexible members 140a and 140b coil, unwanted hair within the threading area enclosed by rotatable flexible members 140a and 140b, along rotatable flexible member 140a is trapped and removed from its follicles. As the rotatable flexible members coil, the slider mechanism 110 moves along the length of the arm 104 in the same direction as the coiling to adjust for the varying tensions in rotatable flexible members 140a and 140b and thereby guides rotatable flexible member 140b to maintain a consistent angle A relative to the rotatable flexible member 140a. This ensures minimal deviation of the coiled rotatable flexible members 140a and 140b from the initial position of rotatable flexible member 140a. Thus, the position of the rotatable flexible member 140a allows for more precise hair removal as it acts as an aid to help the user target removal of unwanted hair.

When the coiling rotatable flexible members 140a and 140b reach a predetermined threshold, the rotational mechanism 130 rotates in the opposite direction causing rotatable flexible members 140a and 140b to uncoil. The predetermined threshold is defined as a limit regulating the coiling in one direction before the rotational mechanism begins to rotate in the opposite direction and includes but is not limited to a torsional tension limit, duration of time, number of rotations, and/or user determined coiling distance or a combination thereof. The preferred embodiments utilize a torsional tension limit. As the rotatable flexible members uncoil, tension in the rotatable flexible members decreases. The slider biasing element 112 assists the slider mechanism 110 to move in the opposite direction along the arm to its initial position. When the rotatable flexible members 140a and 140b uncoil, the removed hair is dislodged from the rotatable flexible members 140a and 140b. The coiling and uncoiling is repeated until the unwanted hair is removed.

The epilation device 100 may comprise a rotational element 142 to connect one end of the rotatable flexible member 140a to the arm connection point 108. The rotational element 142 rotates to reduce torsional tension build up in the rotatable flexible member 140a as the rotatable flexible members are coiled and uncoiled.

The epilation device may also include features to improve visibility during use, such as a light or a magnifying mechanism.

In another embodiment, the movement of the slider mechanism may be controlled mechanically, electronically or combination thereof. Two possible arrangements are shown in FIGS. 5 to 8. The slider biasing element 112 of epilation device 100 may be replaced by a tension control mechanism to apply a greater retracting force on the slider mechanism 110 during uncoiling and a lesser retractile force during coiling. The additional retracting force is useful to overcome resistance by tangled fibres of the rotatable flexible member, trapped hair, and/or obstruction from contact to the user's skin, and the lesser retractile force on the slider mechanism during coiling minimizes deviation of the coiled rotatable flexible members from the original position of rotatable flexible member 140a. A tension control mechanism is defined as any mechanism coupled to rotatable flexible member directly or indirectly to apply greater tension on the rotatable flexible member during uncoiling than during coiling of the flexible member portions.

Figure 5:
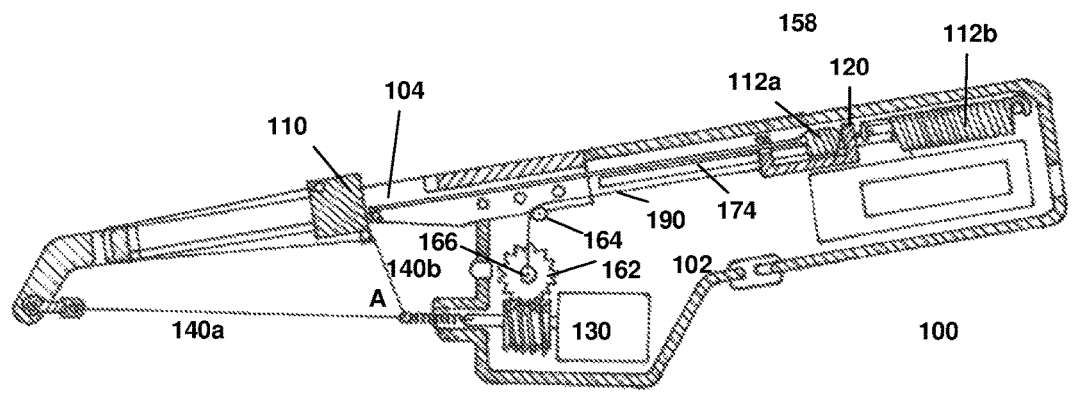
FIG. 5 is a side cross-sectional view of a second embodiment of the epilation device of FIG. 1.
Figure 6:
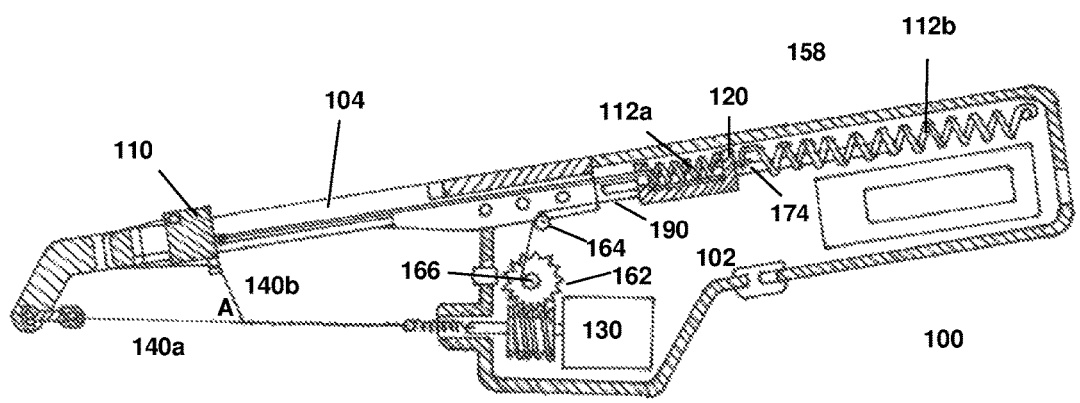
FIG. 6 is a side cross-sectional view of the epilation device of FIG. 5.

Referring to FIGS. 5 and 6, the tension control mechanism is comprised of a gear mechanism 162 coupled to a slider biasing mechanism 158 by a spooling mechanism 166 and a flexible member 190. The gear mechanism has one or more gears. The slider biasing mechanism 158 is comprised of a housing 120 slideable along a track 174, a first slider biasing element 112a, and a second slider biasing element 112b. The housing 120 is movable along the length of body 102. The housing 120 is held under tension by second slider biasing element 112b disposed within the body portion 102. The slider mechanism 110 is held under tension by the slider biasing mechanism 158 via the first slider biasing element 112a. The first slider biasing element 112a is disposed within the housing 120 which allows the housing 120 to regulate the amount of yielding that the first slider mechanism 112a can undergo. In addition first slider biasing element 112a has a lesser retractive force than second slider biasing element 112b. This ensures that when slider mechanism 110 moves in accordance with the coiling of rotatable flexible members 140a and 140b, first slider biasing element 112a will yield prior to the second slider biasing element 112b.

One end of flexible member 190 is connected to the housing 120 and the other end of the flexible member 190 is passed around prong 164 and connected to spooling mechanism 166. Gear mechanism 162 is connected to rotational mechanism 130 and spooling mechanism 166.

When rotational mechanism 130 rotates, rotatable flexible members 140a and 140b coil and gear mechanism 162 rotates. The slider mechanism 110 moves along the length of the arm 104 to adjust for the varying tension and first slider biasing element 112a yields accordingly thereby increasing the retracting force applied on the slider mechanism 110. At the same time, the spooling mechanism 166 rotates in accordance with the rotation of the gear mechanism 162. The flexible member 190 winds around the rotating spooling mechanism 166 and thereby causes the housing 120 to move along the length of the body 102 such that retracting force applied on the slider mechanism 110 is reduced and tension in the second slider biasing element 112b is increased.

When the rotational mechanism 130 rotates in the opposite direction, the rotatable flexible members 140a and 140b uncoil and gear mechanism 162 rotates in the opposite direction. The spooling mechanism 166 also rotates in the opposite direction causing flexible member 190 to unwind from the spooling mechanism 166 and thereby release tension in second biasing element 112b. As second slider biasing element 112b returns to its original position it applies a strong retracting force on housing 120. This increased retracting force on the housing 120 combined with the retracting force in first slider biasing element 112a applies a greater retracting force on the slider mechanism 110, which assists the slider mechanism 110 to move in the opposite direction to its initial position during uncoiling of the rotatable flexible members 140a and 140b.

Figure 7:
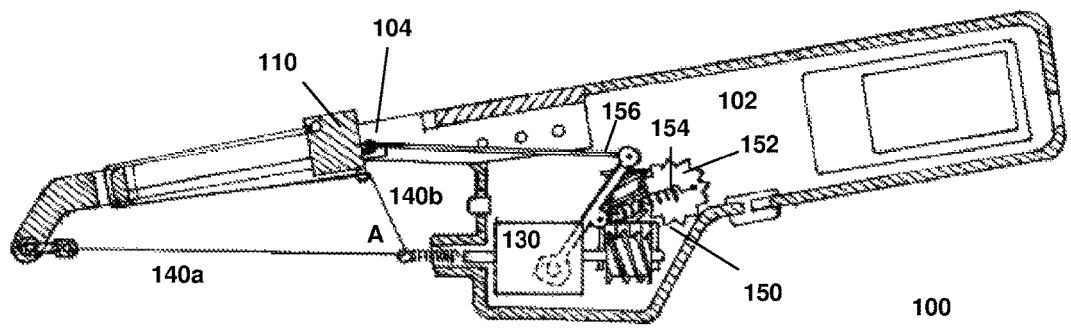
FIG. 7 is a side cross-sectional view of a third embodiment of the epilation device of FIG. 1.
Figure 8:
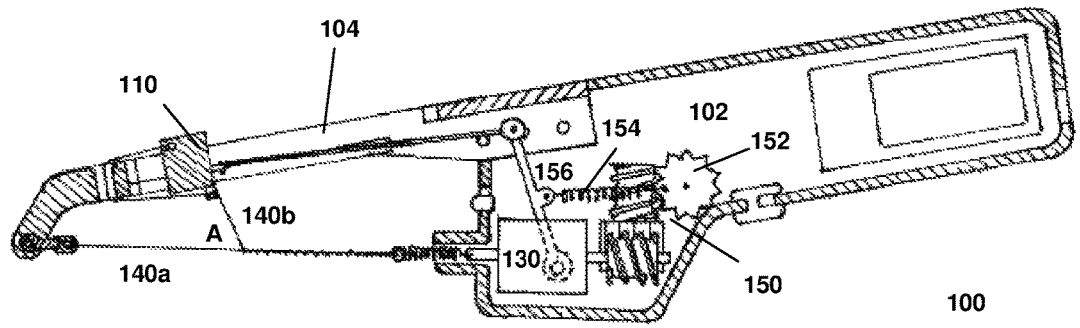
FIG. 8 is a side cross-sectional view of the epilation device of FIG. 7

FIGS. 7 and 8 illustrate another embodiment of a variable tension control mechanism 150 comprised of gear mechanism 152 with one or more gears, a biasing element 154 and a lever mechanism 156 comprising of at least two pivoting arms. The lever mechanism 156 is disposed within body 102. One end is connected to the body 102 and the other end is connected to the slider mechanism 110. The ever mechanism 156 is connected to one end of biasing element 154.

The gear mechanism 152 is connected to the rotational mechanism 130, and the other end of biasing element 154. When rotational mechanism 130 rotates, rotatable flexible members 140a and 140b coil and gear mechanism 152 rotates. The slider mechanism 110 moves along the length of the arm 104 to adjust for the varying tension and the lever mechanism 156 connected to the slider mechanism 110 moves accordingly. Biasing element 154 yields to compensate for the movement of lever mechanism 156 thereby increasing the retracting force applied on the lever mechanism 156 and slider mechanism 110. The biasing element 154 adjusts in accordance with the rotating gear mechanism 152 such that the retracting force applied on the lever mechanism 156 and slider mechanism 110 is reduced. When the rotational mechanism 130 rotates in the opposite direction, the rotatable flexible members 140a and 140b uncoil and gear mechanism 152 rotates in the opposite direction. Biasing element 154 is displaced and yields in the opposite direction to compensate for the rotation of the gear mechanism 152 and tension increases. The increasing tension in the biasing element 154 applies a greater retracting force on the lever mechanism 156 and slider mechanism 110, which assists the slider mechanism 110 to move in the opposite direction along the arm to its initial position during uncoiling of the rotatable flexible members 140a and 140b.

Different shapes and arrangements of the epilation device are possible. One possibility is to use an arm portion that can be nested in a storage position. The arm would slide into an extended position for use. Another possibility is to utilize an arm in a fixed position to the body.

The invention may further comprise pivot mechanisms to minimize the deviation of the coiled rotatable flexible member portions from the initial position of the first rotatable flexible member portion. Deviation of the first rotatable flexible member portion from its initial position results from increased tension during coiling and uncoiling of the first and second portions of the rotatable flexible member. To compensate for the deviation of the first rotatable flexible member portion from its initial position due to increased tension, the pivot mechanism moves in the opposite direction of deviation to maintain the coiled rotatable flexible members along the initial position of the first rotatable flexible member.

FIGS. 9 to 15 illustrate three possible embodiments of pivot mechanisms.

Figure 9:
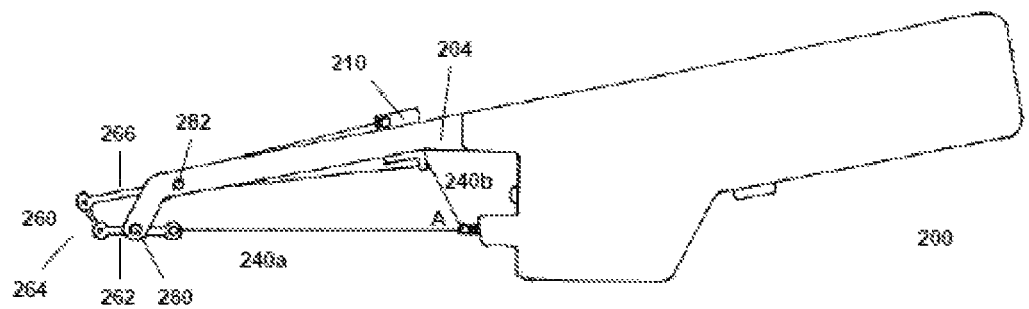
FIG. 9 is a side view of a fourth embodiment of the epilation device.
Figure 10:
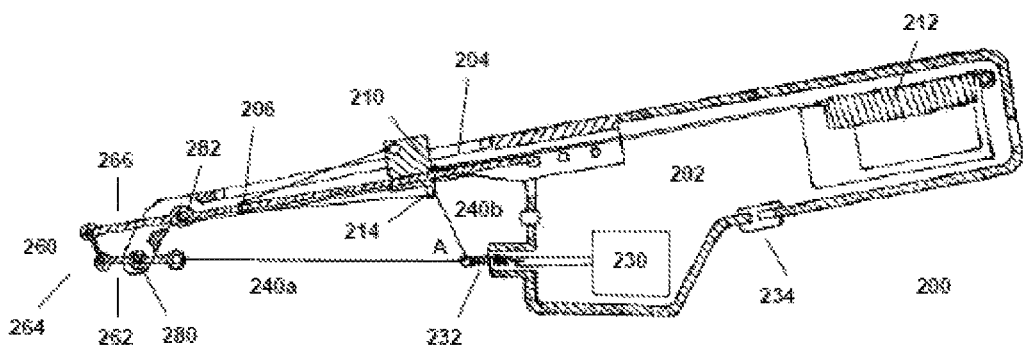
FIG. 10 is a side cross-sectional view of the epilation device of FIG. 9.
Figure 11:
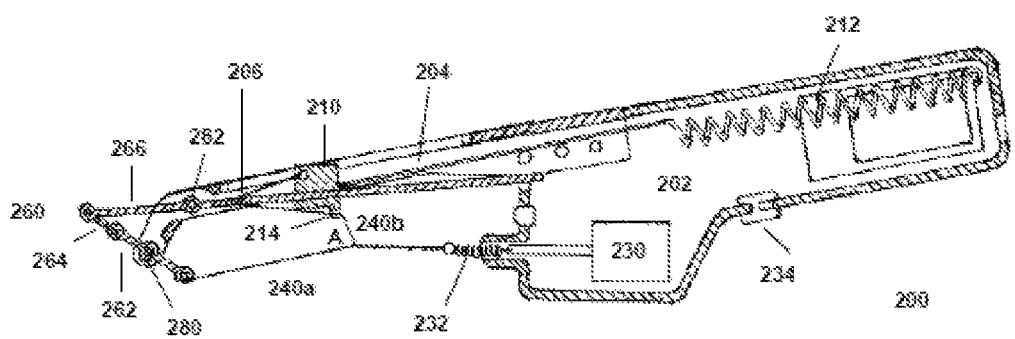
FIG. 11 is a side cross-sectional view of the epilation device of FIG. 9.

One embodiment of a pivot mechanism is shown in FIGS. 9 to 11. The epilation device 200 employs a pivot mechanism 260 that adjusts the rotatable flexible members 240a and 240b to minimize deviation of the coiled rotatable flexible members 240a and 240b from the initial position of rotatable flexible member 240a. The pivot mechanism 260 pivots to compensate for forces applied on the rotatable flexible member 240a during coiling and uncoiling of the rotatable flexible members 240a and 240b to minimize deviation of the coiled rotatable flexible members from the initial position of rotatable flexible member 240a.

Pivot mechanism 260 is comprised of three pivot rods, a lower pivot rod 262, a middle pivot rod 264 and an upper pivot rod 266. The lower pivot rod 262 is connected to the distal end of arm 204 at pivoting connection point 280 for pivoting. The middle pivot rod 264 is connected to the lower pivot rod 262 at one end and the upper pivot rod 266 at the other end. The upper pivot rod 266 is connected to the middle pivot rod 264 at one end and the other end is disposed within the body 202. The upper pivot rod 266 is also connected to arm 204 at pivoting connection point 282 for pivoting. A slider mechanism 210 is movable along the length of the upper pivot rod 266. The slider mechanism is held under tension by a slider biasing element 212 disposed within the body portion 202. The slider biasing element 212 is connected to the slider mechanism 210 to regulate movement of the slider mechanism.

The rotatable flexible member is held under tension by a biasing element 232. One end of a rotatable flexible member is connected to one end of the lower pivot rod 262. The rotatable flexible member is connected to the biasing element 232 to form a first portion of the rotatable flexible member 240a. The biasing element 232 regulates tension of the rotatable flexible member 240a. The rotatable flexible member is passed through slider opening 214 on a lower portion of the slider mechanism 210 to form a second portion of the rotatable flexible member 240b. The rotatable flexible member 240b is further passed through an opening 206 in the upper pivot rod 266 and the other end of the rotatable flexible member is connected to the slider mechanism 210. The rotatable flexible member is connected such that rotatable flexible member 240a has greater tension than rotatable flexible member 240b. This ensures the coiling of rotatable flexible member portions 240a and 240b deviates minimally from the initial position of rotatable flexible member 240b to serve as a guide for precise hair removal.

FIGS. 9 and 10 show the epilation device 200 in an initial position. The user positions the epilation device 200 such that the rotatable flexible members 240a and 240b are positioned on the user's skin over hair that is to be removed and rotatable flexible member 240a is used as a guide for precise hair removal. When a user activates trigger mechanism 234, the rotational mechanism 230 rotates in one direction causing rotatable flexible members 240a and 240b to coil as shown in FIG. 11. When the rotatable flexible members 240a and 240b coil, unwanted hair is trapped and removed from its follicles within the threading area enclosed by rotatable flexible members 240a and 240b, along rotatable flexible member portion 240a. As rotatable flexible member 240b coils with rotatable flexible member 240a, the slider mechanism 210 moves in the same direction of the coiling rotatable flexible members 204a and 240b along the length of the upper pivot rod 266. The slider mechanism 210 and pivot mechanism 260 adjusts for the varying tension to guide the rotatable flexible member 240b to maintain a consistent angle A relative to the rotatable flexible member 240a and minimizes deviation of the coiled rotatable flexible members 240a and 240b from the initial position of rotatable flexible member 240a. Thus, the position of the rotatable flexible member 240a allows for more precise hair removal because it acts as an aid to help the user target removal of unwanted hair. When coiling rotatable flexible members 240a and 240b reaches a predetermined threshold, the rotational mechanism 230 rotates in the opposite direction causing rotatable flexible members 240a and 240b to uncoil. The slider biasing element 212 assists the slider mechanism 210 to move in the opposite direction along the upper pivot rod 266 to its initial position. When the rotatable flexible members 240a and 240b uncoil, the removed hair is dislodged from the rotatable flexible members 240a and 240b. The coiling and uncoiling is repeated until the unwanted hair is removed.

The epilation device 200 may comprise a rotational element to connect one end of the rotatable flexible member 240a to the pivot mechanism 260. The rotational element rotates to reduce torsional tension build up in the rotatable flexible member 240a as the rotatable flexible members are coiled and uncoiled.

Figure 12:
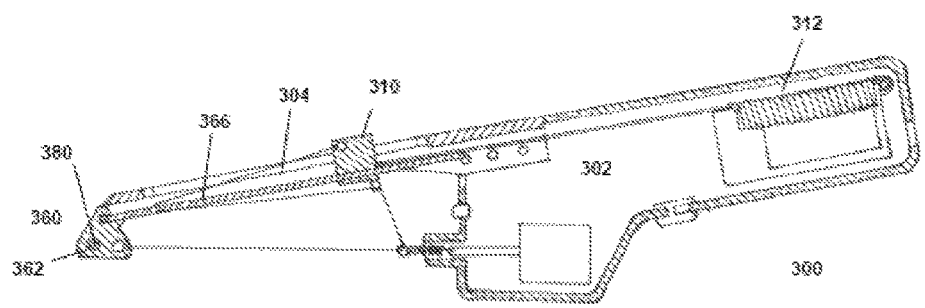
FIG. 12 is a side cross-sectional view of a fifth embodiment of the epilation device.
Figure 13:
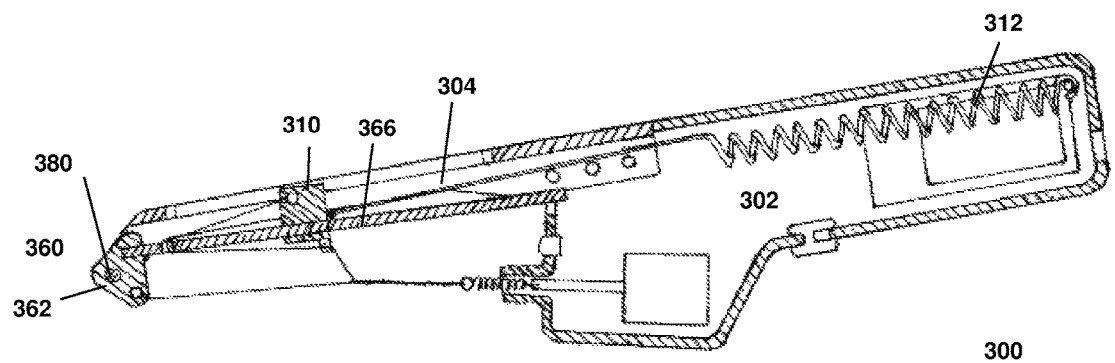
FIG. 13 is a side cross-sectional view of the epilation device of FIG. 12.

FIGS. 12 to 13 show another possible embodiment of the pivot mechanism. The epilation device 300 employs the pivot mechanism 360 comprised of a pivot 362, and a pivot rod 366. The pivot 362 is connected to the distal end of the arm 304 at pivoting connection point 380 for pivoting. The pivot rod 366 is connected to the pivot 362 at one end and the other end is disposed within the body 302. A slider mechanism 310 is movable along the length of the pivot rod 366. The slider mechanism is held under tension by a slider biasing element 312 disposed within the body portion 302. The slider biasing element 312 is connected to the slider mechanism 310 to regulate movement of the slider mechanism.

Figure 14:
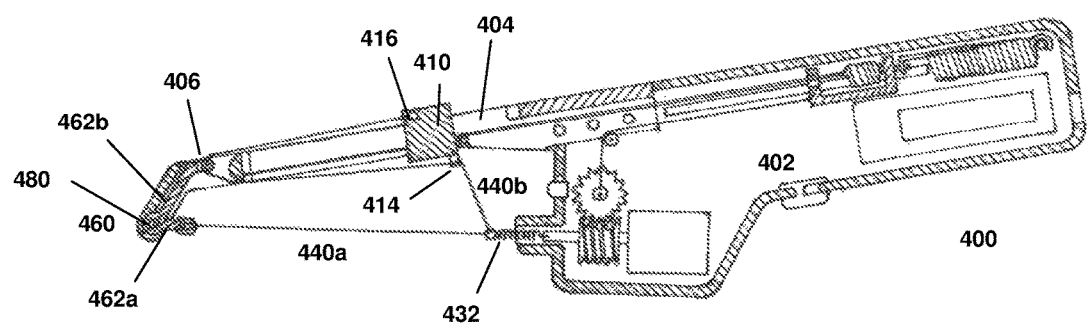
FIG. 14 is a side cross-sectional view of a sixth embodiment of the epilation device.
Figure 15:
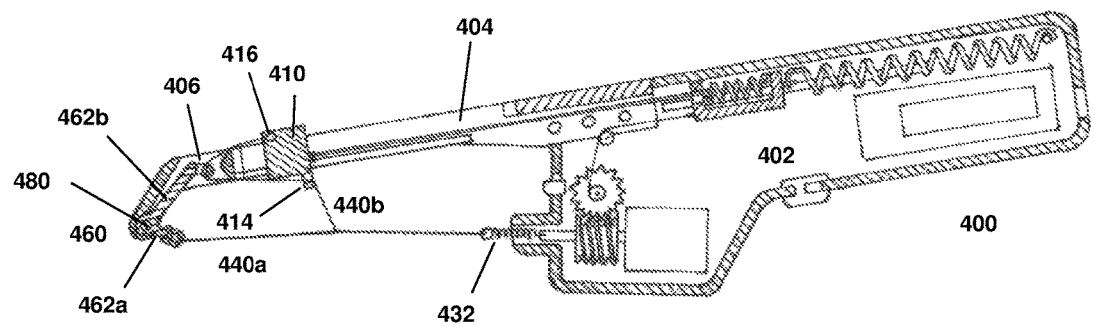
FIG. 15 is a side cross-sectional view of the epilation device of FIG. 14.

FIGS. 14 to 15 show another possible embodiment of the pivot mechanism with the slider mechanism controlled by the variable tension control mechanism described above. The epilation device 400 employs a pivot mechanism 460 comprised of a pivot having two pivot mechanism arms, 462*a* and 462*b*. The pivot is connected to the distal end of the arm 404 at pivoting connection point 480 for pivoting. A slider mechanism 410 is movable along the length of the arm 404. The slider mechanism is held under tension by a variable tension control mechanism (as described above) disposed within the body portion 402.

The rotatable flexible member is held under tension by a biasing element 432. One end of the rotatable flexible member is connected to one end of the pivot mechanism arm 462*a*. The rotatable flexible member is connected to the biasing element 432 to form a first portion of the rotatable flexible member 440*a*. The biasing element 432 regulates tension of the rotatable flexible member 440*a*. The rotatable flexible member is passed through slider opening 414 on a lower portion of the slider mechanism 410 to form a second portion of the rotatable flexible member 440*b*. The rotatable flexible member is further passed through an opening 406 in the pivot mechanism arm 462*b* and the other end of the rotatable flexible member is connected to the slider mechanism 410 at a slider connection point 416. The rotatable flexible member is connected such that rotatable flexible member 440*a* has greater tension than rotatable flexible member 440*b*. This ensures the coiling of rotatable flexible member portions 440*a* and 440*b* deviates minimally from the initial position of rotatable flexible member 440*b* to serve as a guide for precise hair removal.

Another mechanism to maintain a consistent angle between two rotatable flexible member portions, and minimize deviation of a first rotatable flexible member portion, held under greater tension, from its initial position when first and second rotatable flexible member portions are coiled is through the utilization of rotatable rods. FIGS. 16 to 21 illustrate three possible embodiments. A rotatable rod rotates to guide the second portion of the rotatable flexible member during coiling and uncoiling of the rotatable flexible member. As the rotatable rod rotates, a consistent angle A between the two rotatable flexible member portions is maintained and deviation of the first rotatable flexible member portion from its initial position is minimized. This allows the first rotatable flexible member portion to serve as a guide to help a user position the rotatable flexible member portions to more precisely remove unwanted hair, including hard to reach areas.

Figure 16:
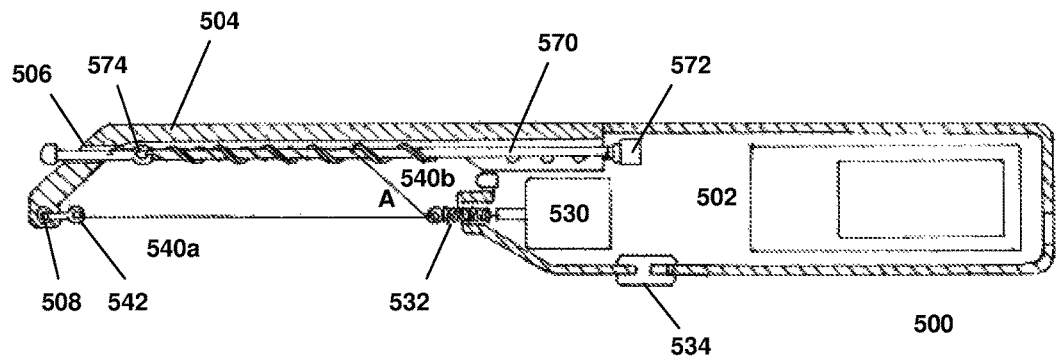
FIG. 16 is a side cross-sectional view of a seventh embodiment of the epilation device.
Figure 17:
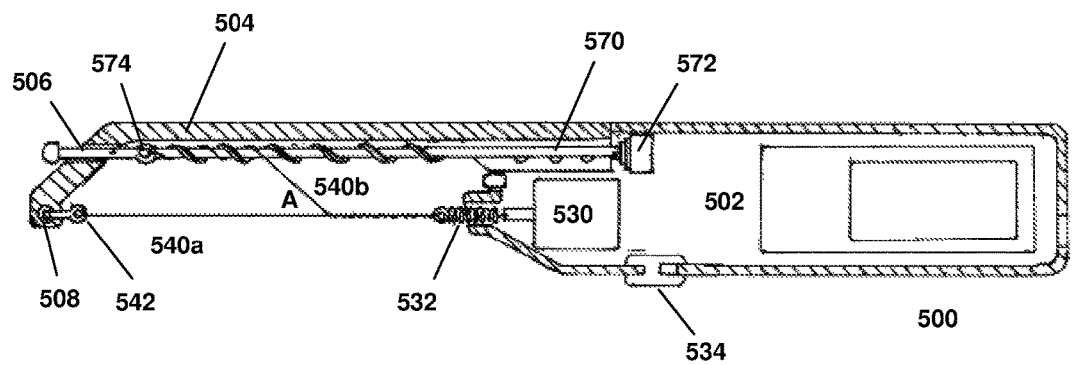
FIG. 17 a side cross-sectional view of the epilation device of FIG. 16.
Figure 18:
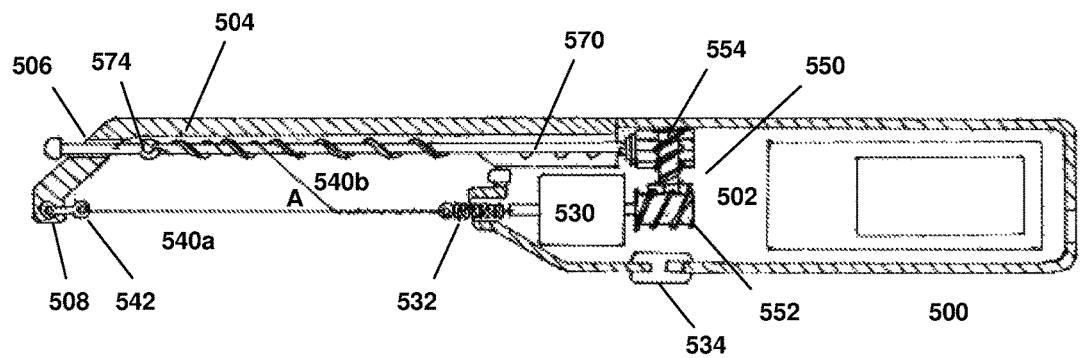
FIG. 18 is a side cross-sectional view of an eighth embodiment of the epilation device of FIG. 16.

FIGS. 16 to 18 illustrate cross-sectional views of two embodiments of a rotatable rod epilation device. The epilation device 500 employs a rotatable rod 570 and includes a body portion 502 and an arm 504 connected to the body portion 502. The arm 504 has an opening 506 for receiving the distal end of the rotating rod.

The rotatable rod 570 has a spiral groove to guide the second rotatable flexible member with a consistent angle A relative to the first rotatable flexible member. Rotatable rod 570 is held under tension by a rod biasing element 572 disposed within the body portion 502. The rod biasing element 572 regulates movement of rotatable rod 570 and includes but is not limited to a coil spring. Rotatable rod 570 can include other mechanisms that can be used to guide the second rotatable flexible member with a consistent angle relative to the first rotatable flexible member including but not limited to a spiral grove.

The rotatable flexible member is held under tension by a biasing element 532. Prior to connecting the rotatable flexible member to the epilation device 500, the rotatable rod 570 is rotated on the distal end to increase torsional tension in the rod. One end of a rotatable flexible member is connected to the tensioned rotatable rod 570 at rod connection point 574. The rotatable rod 570 is released to coil the rotatable flexible member along the spiral groove. Prior to full release of the tensioned state of the rotatable rod 570, the rotatable flexible member is connected to the biasing element 532 to form a second portion of the rotatable flexible member 540*b*. The other end of the rotatable flexible member 540 is connected to the distal end of the arm 504 at an arm connection point 508 to form a first portion of the rotatable flexible member 540*a*. The biasing element 532 regulates tension of the rotatable flexible member 540*a*. The rotatable flexible member is connected such that rotatable flexible member 540*a* has greater tension than rotatable flexible member 540*b*. This ensures the coiled rotatable flexible member portions 540*a* and 540*b* deviate minimally from the initial position of rotatable flexible member 540*a* and serve as a guide for precise hair removal.

The rotatable flexible member is rotatable by a rotational mechanism 530. The rotational mechanism 530 for conveying rotational motion is disposed within the body and connected to a biasing element 532. The rotational mechanism 530 is comprised of a motor, electronics and a power source to provide bidirectional rotation. A trigger mechanism 534 to activate the device is accessible from the outside of the body portion 502.

FIG. 16 shows the epilation device 500 in an initial position. A user positions the epilation device 500 such that the rotatable flexible member 540*a* and 540*b* are positioned on the user's skin over hair that is to be removed and rotatable flexible member 540*a* is used as a guide for precise hair removal. When trigger mechanism 534 is activated, the rotational mechanism 530 rotates in one direction causing rotatable flexible member 540*a* and 540*b* to coil as shown in FIG. 17. When the rotatable flexible members 540*a* and 540*b* coil, unwanted hair is trapped and removed from its follicles within the threading area enclosed by rotatable flexible member 540*a* and 540*b*, along rotatable flexible member portion 540*a*. As rotatable flexible member 540*b* coils with rotatable flexible member 540*a*, the rotatable rod 570 rotates and uncoils the rotatable flexible member 540*b* along the spiral groove of the rotating rod 570 in the same direction of the coiling rotatable flexible members 540*a* and 540*b* to adjusting for the varying tension in the rotatable flexible members and guide the rotatable flexible member 540*b* to maintain a consistent angle A relative to the rotatable flexible member 540*a* and minimize deviation of the coiled rotatable flexible members from the initial position of rotatable flexible member 540*a*. Thus, the position of the rotatable flexible member 540*a* allows for more precise hair removal because it acts as an aid to help the user target removal of unwanted hair.

When the coiling rotatable flexible members 540a and 540b reach a predetermined threshold, the rotational mechanism 530 begins to rotate in the opposite direction causing rotatable flexible members 540a and 540b to uncoil and rotatable flexible member portion 540b to coil again along the spiral groove of the rotatable rod 570. The rod biasing element 572 assists the rotatable rod 570 to rotate in the opposite direction to its initial position as depicted in FIG. 16. When the rotatable flexible member portions 540a and 540b uncoil, the removed hair is dislodged from the rotatable flexible members 540a and 540b. The coiling and uncoiling is repeated until the unwanted hair is removed.

The epilation device 500 may comprise a rotational element 542 to connect one end of the rotatable flexible member 540a to the arm connection point 508. The rotational element 542 rotates to reduce torsional tension build up in the rotatable flexible member 540a as the rotatable flexible members are coiled and uncoiled.

The epilation device may also include features to improve visibility during use, such as a light that is activated by trigger mechanism or a magnifying mechanism.

In another embodiment, the rotational biasing element 572 of epilation device 500 may be replaced by a tension control mechanism as described above to apply a rotational retracting force on the rotating rod 570 during uncoiling. The additional rotational retracting force is useful to overcome resistance by tangled fibres of the rotatable flexible member, trapped hair, and/or obstruction from contact to the user's skin.

Referring to FIG. 18, the tension control mechanism 550 is comprised of gear mechanism 552 with one or more gears and a biasing element 554. The biasing element 554 is connected to rotatable rod 570. Gear mechanism 552 is connected to rotational mechanism 530, and biasing element 554. When rotational mechanism 530 rotates, rotatable flexible members 540a and 540b coil and gear mechanism 552 rotates. Biasing element 554 adjusts to compensate for the rotating gear mechanism 552 such that the torsional force applied on the rotating rod 570 is reduced. When rotational mechanism 530 rotates in the opposite direction, rotatable flexible members 540a and 540b uncoil and gear mechanism 552 rotates in the opposite direction. Biasing element 554 yields to compensate for the rotating gear mechanism 552 such that the torsional force applied on rotatable rod 570 increases. The increasing tension in biasing element 554 applies a greater torsional force on rotatable rod 570, which assists rotatable rod 570 in rotating in the opposite direction to reach its initial position during uncoiling of the rotatable flexible members 540a and 540b.

Figure 19:
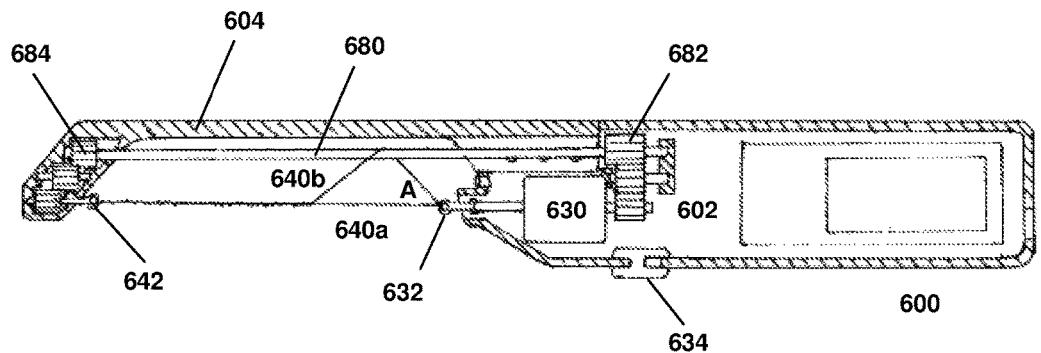
FIG. 19 is a side cross-sectional view of a ninth embodiment of the epilation device.
Figure 20:
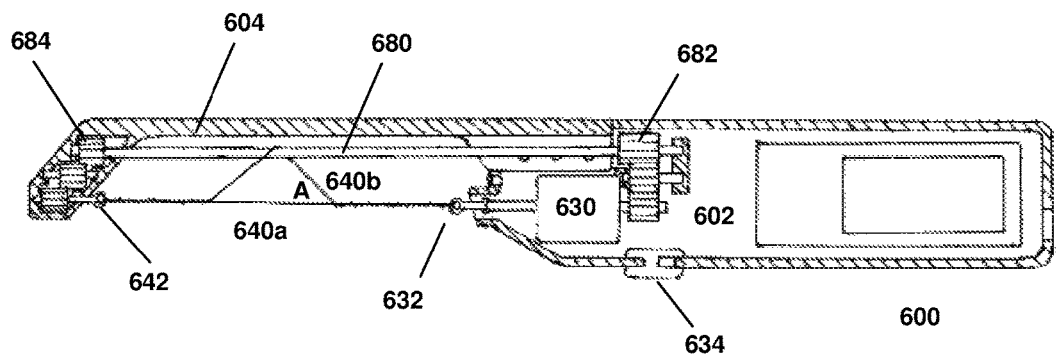
FIG. 20 is a side cross-sectional view of the epilation device of FIG. 19.
Figure 21:
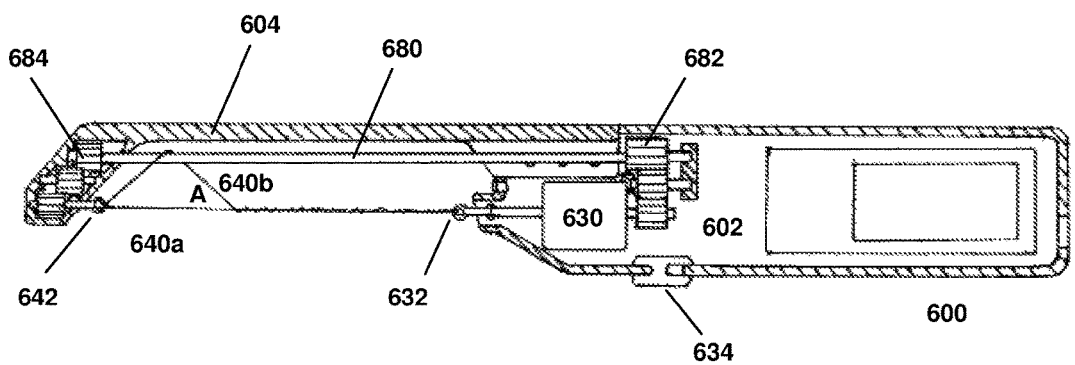
FIG. 21 is a side cross-sectional view of the epilation device of FIG. 19.

Another embodiment of the rotatable rod is shown in FIGS. 19 to 21. The epilation device 600 employs a rotatable rod 680 and a pair of gear mechanisms 682 and 684 to maintain a consistent angle A between the two rotatable flexible member portions and minimize deviation of the coiled rotatable flexible members from the initial position of rotatable flexible member 640a. The epilation device 600 includes a hand-held body portion 602 and an arm 604 connected to the body portion 602. A rotational mechanism 630 for conveying rotational motion is disposed within the body 602 and connected to a first gear mechanism 682 disposed within the body 602. The rotational mechanism 630 may be comprised of a motor, electronics and a power source to provide bidirectional rotation. A trigger mechanism 634 to control the rotational mechanism 630 is accessible from the outside of the body portion 602. The proximal end of the rotatable rod 680 is connected to the body portion 602 by a first gear mechanism 682 disposed within the body 602. The distal end of the rotatable rod 680 is connected to the arm 604 by a second gear mechanism 684 disposed within the distal end of the arm 604.

The rotatable flexible member is connected to connection point 632 located on rotational mechanism 630 at one end. The rotatable flexible member 640 is then connected to the second gear mechanism 684 at connection point 642 to form a first portion of the rotatable flexible member 640a. The other end of the rotatable flexible member is coiled around the first portion of the rotatable flexible member 640a to form a pre-coiled section, then looped over rotatable rod 680, and connected to connection point 632 to form a second portion of the rotatable flexible member 640b. The rotatable flexible member is held under tension with first rotatable flexible member 640a held under greater tension than second rotatable flexible member 640b. This ensures the coiling of rotatable flexible members 640a and 640b deviates minimally from the initial position of rotatable flexible member 640a and serves as a guide for precise hair removal.

FIG. 19 shows the epilation device 600 in an initial position. A user positions the epilation device 600 such that the rotatable flexible members 640a and 640b are positioned on the user's skin over hair that is to be removed and rotatable flexible member 640a is used as a guide for precise hair removal. When trigger mechanism 634 is activated, rotational mechanism 630 rotates in one direction causing first gear mechanism 682, second gear mechanisms 684, and rotatable rod 680 to rotate. The rotatable flexible members 640a and 640b closest to the connection point 632 coil and pre-coiled rotatable flexible members 640a and 640b closest to second gear mechanism 684 uncoil. When rotatable flexible member portions 640a and 640b coil, unwanted hair is trapped and removed from its follicles within the threading area enclosed by rotatable flexible member 640a and 640b, along rotatable flexible member portion 640a. The simultaneous coiling of the rotatable flexible members 640a and 640b on one side of the looped section of second rotatable flexible member 640b and uncoiling of the rotatable flexible members 640a and 640b on the other side of the looped section as depicted in FIG. 20 reduces tension in the rotatable flexible members 640a and 640b. The looped portion of rotatable flexible member 640b moves along the length of the rotating rod 680 to guide rotatable flexible member 640b and maintain a consistent angle A relative to rotatable flexible member 640a and minimize deviation of the coiled rotatable flexible members from the initial position of rotatable flexible member 640a. Thus, the position of rotatable flexible member 640a allows for more precise hair removal as it acts as an aid to help the user target removal of unwanted hair.

When the coiling rotatable flexible members 640a and 640b reach a predetermined threshold as depicted in FIG. 21, rotational mechanism 630 begins to rotate in the opposite direction causing rotatable flexible members 640a and 640b closest to connection point 632 to uncoil and rotatable flexible members 640a and 640b closest to second gear mechanism 684 to coil. When the rotatable flexible member portions 640a and 640b uncoil, the removed hair is dislodged from rotatable flexible members 640a and 640b. The coiling and uncoiling is repeated until the unwanted hair is removed.

In some embodiments rotatable flexible member may be held under tension by a biasing element connected to rotational mechanism 630.

The foregoing description illustrates only certain preferred embodiments of the invention. The invention is not limited to the foregoing examples. That is, persons skilled in the art will appreciate and understand that modifications and variations are, or will be, possible to utilize and carry out the teachings of the invention described herein. Accordingly, all suitable modifications, variations and equivalents may be resorted to, and such modifications, variations and equivalents are intended to fall within the scope of the invention as described and within the scope of the claims.

What is claimed is:

1. An epilation device comprising:
a body portion;
one arm connected to the body portion;
a slider mechanism held under tension; and
a rotatable flexible member having a first and a second portion, the rotatable flexible member directly attached to the arm at one end and the slider mechanism at the other end, the rotatable flexible member held under tension, and the rotatable flexible member attached to the slider mechanism with the first portion held under greater tension than the second portion to maintain a consistent angle of the second portion relative to the first portion, and to minimize deviation of the first portion from an initial position of the first portion when the first portion and second portion are coiled;
wherein when the rotatable flexible member rotates, first and second portions of the rotatable flexible member coil and uncoil relative to the direction of rotation along the first portion of the rotatable flexible member; and
wherein the first portion of the rotatable flexible member serves as a guide for precise hair removal.

2. The epilation device of claim 1 further comprising a pivot mechanism that serves to connect the rotatable flexible member to the arm and balance varying tension of the rotatable flexible member.

3. The epilation device of claim 2 further comprising a rotational element that serves to connect the rotatable flexible member to the arm to reduce torsional tension build up in the coiling and uncoiling of the rotatable flexible member.

4. The epilation device of claim 1 further comprising a rotational element that serves to connect the rotatable flexible member to the arm to reduce torsional tension build up in the coiling and uncoiling of the rotatable flexible member.

5. The epilation device of claim 4, wherein the rotatable flexible member is held under tension by a biasing element.

6. The epilation device of claim 1, wherein the slider mechanism is held under tension by a tension control mechanism.

7. The epilation device of claim 1, wherein the rotatable flexible member is held under tension by a biasing element.

* * * * *